(12) United States Patent
Meruva et al.

(10) Patent No.: US 9,019,500 B2
(45) Date of Patent: Apr. 28, 2015

(54) HEAT LAMP TEST FOR IDENTIFICATION OF OIL SPOTS

(71) Applicant: Altria Client Services Inc., Richmond, VA (US)

(72) Inventors: Narendra K. Meruva, Midlothian, VA (US); Christopher B. McFarlane, Richmond, VA (US); Jennifer H. Smith, Chesterfield, VA (US)

(73) Assignee: Altria Client Services Inc., Richmond, VA (US)

( * ) Notice: Subject to any disclaimer, the term of this patent is extended or adjusted under 35 U.S.C. 154(b) by 0 days.

(21) Appl. No.: 13/730,424

(22) Filed: Dec. 28, 2012

(65) Prior Publication Data

US 2014/0185039 A1    Jul. 3, 2014

(51) Int. Cl.
*G01N 21/88* (2006.01)
*A24C 5/34* (2006.01)

(52) U.S. Cl.
CPC .......... *G01N 21/8803* (2013.01); *A24C 5/3412* (2013.01)

(58) Field of Classification Search
USPC ............ 356/429–431, 23; 131/284, 905, 907; 430/466, 403, 404; 250/559.16, 250/559.01, 559.29
See application file for complete search history.

(56) References Cited

U.S. PATENT DOCUMENTS

| | | | |
|---|---|---|---|
| 4,616,139 A | 10/1986 | Heitmann | |
| 4,639,592 A | 1/1987 | Heitmann | |
| 5,092,349 A | 3/1992 | Smith et al. | |
| 5,228,462 A | 7/1993 | Osmalov et al. | |
| 5,414,270 A | 5/1995 | Henderson et al. | |
| 5,450,863 A * | 9/1995 | Collins et al. | 131/365 |
| 5,729,343 A * | 3/1998 | Aiyer | 356/504 |
| 6,020,969 A * | 2/2000 | Struckhoff et al. | 356/430 |
| 6,191,430 B1 * | 2/2001 | Belotserkovsky et al. | 250/559.16 |
| 6,213,128 B1 | 4/2001 | Smith et al. | |
| 6,733,960 B2 * | 5/2004 | Nash et al. | 430/466 |
| 6,929,013 B2 * | 8/2005 | Ashcraft et al. | 131/365 |
| 7,117,871 B2 * | 10/2006 | Hancock et al. | 131/65 |
| 8,069,859 B2 * | 12/2011 | Minami et al. | 131/284 |
| 2001/0050772 A1 * | 12/2001 | Meinlschmidt et al. | 356/430 |
| 2003/0150466 A1 | 8/2003 | Kitao et al. | |
| 2006/0207616 A1 | 9/2006 | Hapke et al. | |
| 2007/0137661 A1 | 6/2007 | Siems | |
| 2007/0175058 A1 | 8/2007 | Binge | |
| 2009/0196039 A1 * | 8/2009 | Shyu et al. | 362/253 |
| 2010/0165344 A1 * | 7/2010 | Kokko et al. | 356/429 |
| 2013/0003063 A1 * | 1/2013 | Headley et al. | 356/402 |

* cited by examiner

*Primary Examiner* — Sang Nguyen
(74) *Attorney, Agent, or Firm* — Roberts Mlotkowski Safran & Cole, P.C.

(57) ABSTRACT

A system for differentiating between oil spots and non-oil spots in a wrapped article comprising a web and a wrapped material. The system includes a heat source that applies heat to a wrapped article for a predetermined amount of time when the wrapped article is placed in a sample area on a surface that is arranged at a predetermined distance away from a heating element of the heat source; and a light source that provides backlighting to the web of the wrapped article when the web has been separated from the wrapped material and placed on a viewing surface of the light source. A method for differentiating between oil spots and non-oil spots in wrapped articles and a field test kit are also provided.

38 Claims, 2 Drawing Sheets

HEAT LAMP TEST FOR IDENTIFICATION OF OIL SPOTS

FIELD

Disclosed herein are methods and systems for inspecting manufactured cigarettes and, more particularly, to visually inspecting finished cigarettes for oil spots.

SUMMARY

Quality control systems and methods are commonly employed for maintaining standards in manufactured products. Typically, such systems involve the periodic inspection of randomly selected samples of the manufactured product in order to assess whether they comply with one or more predetermined requirements. Depending on the degree or extent of compliance, the identification of a nonconforming sample of the manufactured product may lead to a quantity of the product being rejected, the manufacturing process being adjusted, and/or to the replacement of manufacturing equipment or raw materials.

During the manufacture of cigarettes, the outer surface of randomly selected cigarettes is typically inspected as part of a visual quality audit in order to identify and assess non-conformities such as, for example, tears or stains on the wrapper. Such inspections are for quality control and are intended to uncover unsatisfactory conditions in the cigarettes, such as stem holes, skewed or torn tipping, tobacco under the rod seam, torn ends on the cigarette, and spots from glue, flavors or oil.

Tobacco smoking articles, such as cigarettes, are made into rods on machines which take cut filler that is formed into a continuous rod of tobacco, and encircles the tobacco with a continuous ribbon of paper which is glued and heat-sealed. The continuous tobacco rod is formed and sealed in the maker machine and then proceeds to another processing machine, such as a tipper. The tipper attaches a filter plug cut to the appropriate length between two tobacco rods. The tipper applies glue and wraps tipping paper around the filter segment and a portion of the tobacco rods. This creates a double length cigarette. The two cigarettes are then cut and oriented into a single row. It is the completed cigarette at the end of this production line that is inspected for unsatisfactory conditions, i.e., non-conformities such as oil spots on the cigarette paper.

The cigarette manufacturing process involves complex machinery, such as those described above, with a great number of moving parts that require lubrication for normal operation. Although extremely rare, lubricants from the manufacturing machinery may inadvertently come into contact with the components of the cigarette during the manufacturing process, resulting in spots or stains on the cigarette paper. The spots or stains on the cigarette paper may be visible to the naked eye and provide an unacceptable appearance to the cigarette.

Typically when a spot is found on a finished cigarette during random visual inspection at the end of the production line, the spotted cigarette is further analyzed, e.g., to determine the content of the material forming the spot. Such random visual inspection to identify nonconforming articles and subsequent analysis of nonconforming articles is used to improve the quality of all of the manufactured articles, e.g., by identifying and eliminating the source of the spot.

It has been found that some spots appearing on the paper of a finished cigarette are not caused by machinery lubricant, but rather are from other sources. For example, a yellowish and/or brownish spot may appear on the paper as a result of moisture that has migrated from the tobacco to the paper. As another example, flavor additives can cause a spot to appear on the paper of the finished cigarette. While spots from tobacco staining and/or flavor additives may produce an undesirable appearance, spots from these sources are not as objectionable as a spot that might occur from a machinery lubricant, e.g., an oil spot.

It is costly to analyze nonconforming samples that have been flagged during a visual inspection at the end of a production line. For example, spotted cigarettes identified during visual inspections are typically further analyzed using various laboratory tests, such as gas chromatography-mass spectrometry (GC-MS). However, the additional analysis is costly in that it involves employee time and the procurement, operation, and maintenance of specific lab equipment, such as GC-MS systems.

Moreover, the identification of spots in finished cigarettes during random visual inspection at the end of the production line may cause all the product in that manufacturing lot to be put on hold pending the results of the additional analysis. Additionally, the manufacturing machinery in which the nonconforming samples were produced may be temporarily shut down pending the results of the additional analysis.

In accordance herewith, there is provided a system and method that is used to differentiate between lubricant spots and non-lubricant spots on wrapped articles comprising a web and a wrapped material, such wrapped articles including, but not limited to, finished cigarettes, during visual inspection at the end of a production line. Embodiments disclosed herein provide a quick field test that can be easily performed at or near the end of the production line, or even in the marketplace, to distinguish between oil spots and non-oil spots. In embodiments, cigarettes having non-oil spots are not subject to further analysis since non-oil spots are low-level nonconformities caused by water and/or flavor solution components such as alcohol, propylene glycol, glycerin, etc. In this manner, implementations disclosed herein reduce the number of nonconforming articles submitted for further analysis, thus providing a savings in terms of lab costs regarding such analyses. Moreover, by providing the ability of at-line decision making on whether to submit nonconforming articles for further analysis, implementations disclosed herein reduce manufacturing down time and reduce the amount of product on hold.

According to a first aspect, there is a system for differentiating between oil spots and non-oil spots in finished cigarettes. The system includes a heat source that applies heat to a cigarette for a predetermined amount of time when the cigarette is placed in a sample area on a surface that is arranged at a predetermined distance away from a heating element of the heat source, wherein the cigarette is a finished cigarette comprising paper wrapped around a tobacco portion; and a light source that provides backlighting to the paper of the cigarette when the paper has been separated from the tobacco portion and placed on a viewing surface of the light source.

According to another aspect, there is provided a method for differentiating between oil spots and non-oil spots in finished cigarettes. The method includes the steps of obtaining a finished cigarette from a production line, wherein the finished cigarette comprises paper wrapped around a tobacco portion; detecting a visible spot on the paper; drying the cigarette using a heat source for a predetermined amount of time; and visually inspecting the cigarette for the spot after the drying.

According to a further aspect, there is provided a field test kit for differentiating between oil spots and non-oil spots in finished cigarettes. The field test kit includes a heat source that applies heat to a cigarette for a predetermined amount of time when the cigarette is placed in a sample area on a surface that is arranged at a predetermined distance away from a heating element of the heat source, wherein the cigarette is a finished cigarette comprising paper wrapped around a tobacco portion; and a light source that provides backlighting to the paper of the cigarette when the paper has been separated from the tobacco portion and placed on a viewing surface of the light source.

BRIEF DESCRIPTION OF THE DRAWINGS

Various aspects are further described in the detailed description which follows, in reference to the noted plurality of drawings by way of non-limiting examples of embodiments, in which like reference numerals represent similar parts throughout the several views of the drawings.

DETAILED DESCRIPTION

This disclosure relates generally to inspecting wrapped articles comprising a web and a wrapped material, such wrapped articles including, but not limited to, manufactured cigarettes and, more particularly, to visually inspecting finished cigarettes for oil spots. According to aspects disclosed herein, a finished cigarette is randomly picked from the end of the production line and visually inspected for visible spots on the cigarette paper. In embodiments, a cigarette having a spot is subjected to a drying process and subsequently re-inspected. A spot that disappears upon being subjected to the drying process is identified as a non-oil spot. When a spot remains after the drying process, the tobacco is removed from the paper and the paper is viewed against a light source. Spots that cause the paper to appear transparent and/or translucent against the light source are identified as oil spots, whereas spots that do not cause the paper to appear transparent and/or translucent against the light source are identified as non-oil spots. Only cigarettes identified as having an oil spot are flagged for further analysis. In this manner, implementations disclosed herein provide a system and method for a field test for differentiating between oil spots and non-oil spots in finished cigarettes and, thus, advantageously reduce costs, manufacturing machine downtime, and product hold time.

Figure 1:
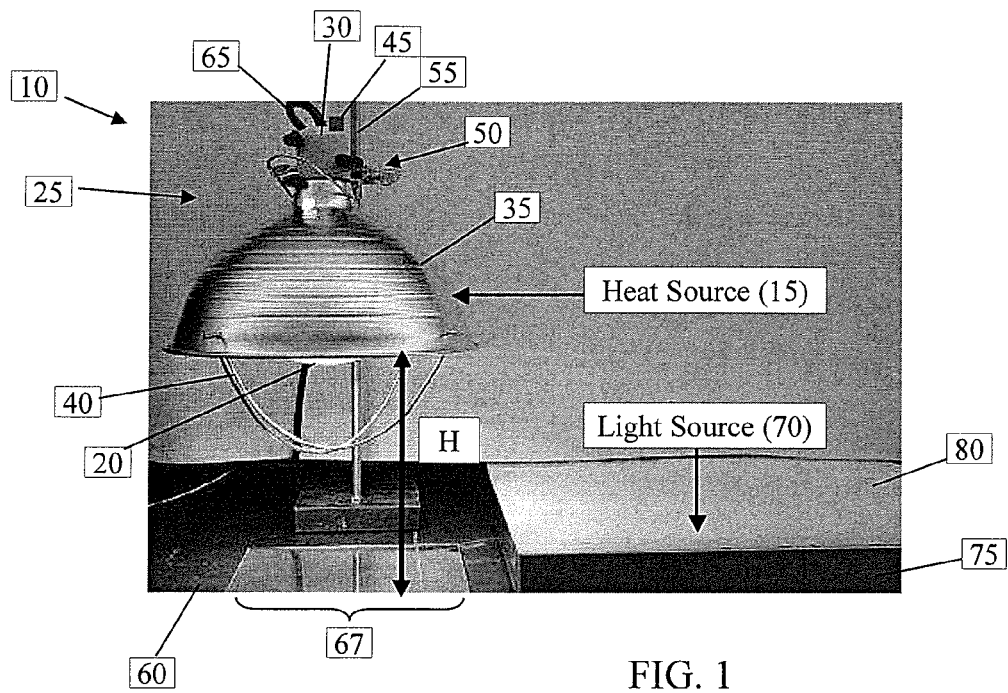
FIG. 1 shows a system for differentiating between oil spots and non-oil spots in finished cigarettes in accordance herewith.

FIG. 1 shows a system 10 for differentiating between oil spots and non-oil spots in finished cigarettes in accordance herewith. In embodiments, the system 10 includes a heat source 15 that is used in a drying process during a field test of finished cigarettes. The heat source 15 may include any suitable arrangement of elements configured to carry out the drying process, as described in greater detail herein. In an exemplary non-limiting embodiment, the heat source 15 includes a heat lamp including a bulb 20 and a fixture 25. The bulb 20 may be, for example, a heat lamp bulb comprising a clear, 250 watt, 120 volt incandescent light bulb, although other types of bulbs may be used within the scope of this disclosure. The bulb 20 generates heat when turned on and thus functions as a heating element of the heat source 15.

In embodiments, the fixture 25 includes a threaded porcelain socket 30 for receiving a threaded end of the bulb 20, a shroud 35, a safety guard 40, a switch 45, and a connecting mechanism 50 for selectively connecting the fixture 25 to a support 55. The shroud 35 may be connected to the socket 30 and/or mechanism 50 and may be composed of a light-weight metal, such as aluminum, tin, etc., that reflects a portion of the light emanating from the bulb 20. The shroud 35 may have any suitable size and shape, and in embodiments has a circular shape with a base diameter of about 10.5 inches and walls that taper conically from the base diameter to the socket 30.

The guard 40 may comprise one or more structural elements connected to the shroud 35 that inhibit a user from inadvertently touching the bulb 20. The switch 45 may be integral with or connected to the socket 30 and is configured to provide a switching mechanism for selectively applying electricity to the bulb 20 via the socket 30. The fixture 25 may further include an electrically conductive flexible elongate element, such as an insulated cord 65, that is electrically connected to the switch 45 at a first end and has a structure for connecting to a power source at a second end opposite the first end.

The connecting mechanism 50 may include a clamp or other equivalent mechanism for selectively connecting the fixture 25 to the support 55, such that a distance "H" between the bulb 20 and a surface 60 can be adjusted. In embodiments, the distance "H" is about eight inches and the surface 60 includes a defined sample area 67 substantially centered on and directly opposed from the bulb 20. In further embodiments, the sample area 67 is about five inches by about five inches square, and is capable of containing more than one finished cigarette. In this manner, plural cigarettes may be subject to the drying process at a same time using a single heat source 15. It is to be understood that the system is not limited to the particular fixture 25 described herein, and that other suitable fixtures may be used to house the bulb within the scope of this disclosure.

In accordance herewith, the heat source 15 is used in a drying process for a finished cigarette that is found to have a spot during a visual inspection, as described in greater detail herein. For example, a cigarette having a spot may be placed on the surface 60 under the heat source 15 with the bulb 20 turned on. This arrangement applies heat to the paper of the cigarette and provides an opportunity for the spot to disappear, e.g., through evaporation of the liquid substance causing the spot.

Still referring to FIG. 1, the system 10 additionally includes a light source 70. In embodiments, the light source 70 comprises a light box including a base 75, at least one fluorescent tube (not shown) housed within the base 75, and a viewing surface 80 connected to the base 75 and over the at least one fluorescent tube. The light box may be constructed of any suitable materials. For example, the base 75 may include a housing and/or frame composed of corrosion resistant stainless steel, plastic, etc. The viewing surface 80 may be composed of any suitable material that transmits and diffuses the light emanating from the at least one fluorescent tube. In embodiments, the viewing surface 80 comprises translucent acrylic having a substantially white color.

In accordance herewith, the light source 70 is used to visually re-inspect the spotted cigarette after the drying process has been performed with the heat source 15, as described in greater detail herein. For example, when a cigarette still has a visible spot after being subjected to the drying process using the heat source 15, the paper of the cigarette is separated from the tobacco and placed on the viewing surface 80 of the light source 70 such that the light of the at least one fluorescent tube transmits through the viewing surface 80 and the paper. While in this configuration, the spotted area of the paper is compared to a non-spotted area of the same paper for determining whether the spotted area has a translucent and/or transparent appearance relative to the non-spotted area.

Figure 2:
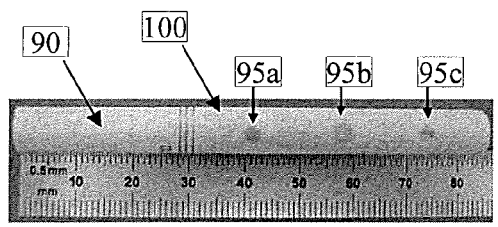
FIG. 2 shows a spotted cigarette prior to drying in accordance herewith.

FIG. 2 shows a cigarette 90 having three spots 95*a*, 95*b*, and 95*c* visible on the paper 100. The cigarette 90 represents a finished cigarette that has been randomly selected from the manufacturing machinery at the end of the production line, e.g., for a visual inspection for quality control. In embodiments, the cigarette 90 is placed on the surface 60 described in FIG. 1 with the spots 90*a-c* facing upward toward the bulb 20 with the bulb 20 turned on. According to aspects disclosed herein, the distance "H" is about eight inches and the cigarette 90 is left in this drying configuration for at least one minute. In accordance herewith, the drying process provides an opportunity for any non-oil based spots to evaporate from the paper of the cigarette 90, thus providing a technique for differentiating between oil spots and non-oil spots on the finished cigarette.

Figure 3:
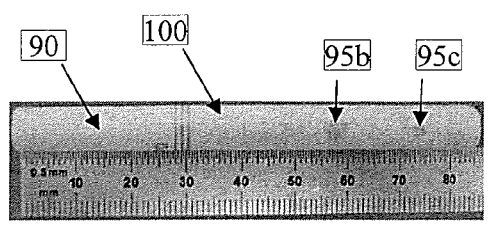
FIG. 3 shows the spotted cigarette after drying in accordance herewith.

FIG. 3 shows the cigarette 90 after the drying process, e.g., after being placed on the surface 60 under the lit bulb 20 with the spots 95*a-c* pointing upward toward the lit bulb 20 for at least one minute. The spot 95*a* is no longer visible on the cigarette 90 in FIG. 3, thus indicating that the spot 95*a* was caused by a non-oil substance such as a water and/or flavor solution prepared in alcohol, propylene glycol, glycerin, etc.

Figure 4:
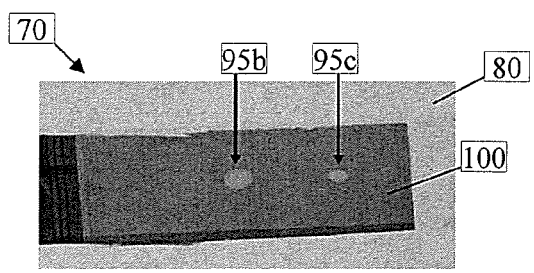
FIG. 4 shows the spotted cigarette paper backlit by a light source in accordance herewith.

However, spots 95*b* and 95*c* remain visible on the cigarette 90 in FIG. 3, e.g., after the drying process. In accordance herewith, as a result of at least one spot still being visible after the drying process, the paper 100 is separated from the tobacco and placed on the viewing surface 80 of the light source 70, e.g., as shown in FIG. 4. The paper 100 may be removed from the tobacco in any suitable manner, such as by slitting the paper 100 with a razor or knife and removing the tobacco.

As shown in FIG. 4, spots 95*b* and 95*c* have a translucent and/or transparent appearance with respect to other non-spotted areas of the paper 100 when backlit by the light source 70. The translucent and/or transparent appearance indicates that the spots 95*b* and 95*c* might be caused by oil such as food grade lubricant or machine lubricant. As such, the cigarette 90 may be flagged for further analysis, such as nonconforming product investigation and lab analysis to determine the source of the spots.

Figure 5:
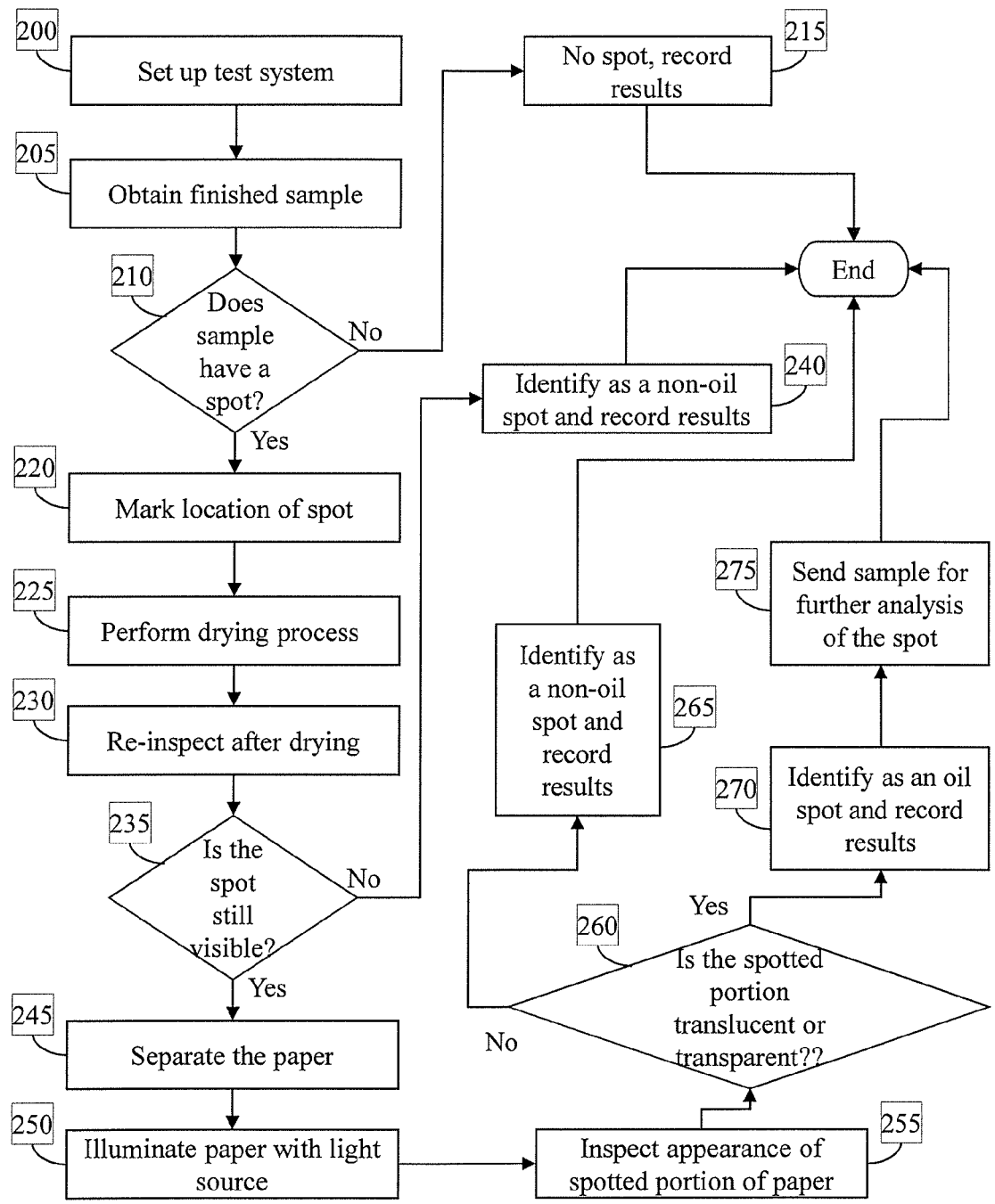
FIG. 5 shows a flow diagram of a quality control method in accordance herewith.

FIG. 5 shows a flow diagram of a method for differentiating between oil spots and non-oil spots in finished cigarettes in accordance herewith. Methods in accordance herewith may be performed using the system 10 described with respect to FIG. 1 and in a manner similar to that described with respect to FIGS. 2-4, or equivalents. The method is described with respect to a single cigarette, although it is to be understood that the method may be performed simultaneously with plural cigarettes. Moreover, the method is described with respect to a single spot on a cigarette, although it is to be understood that the method may be performed with a cigarette having more than one spot.

At step 200, a system is set up for performing a visual inspection of at least one cigarette. In embodiments, the set up step includes obtaining and configuring the system 10 described with respect to FIG. 1, e.g., a heat source 15 and a light source 70. The set up step may further include: adjusting the height "H" of the bulb 20 to about eight inches above the surface 60; defining the sample area 67; turning on the bulb 20; and waiting for about 30 minutes or more after turning on the bulb for the bulb to equilibrate to achieve a substantially constant heat output. The system 10 may be set up at or very near the end of a production line of machinery that manufactures finished cigarettes.

At step 205, a finished cigarette is obtained from the manufacturing machinery in a conventional manner. At step 210, the cigarette is visually inspected for visible spots on the paper. When no spots are visible on the paper, then at step 215 the cigarette is identified as a conforming sample, e.g., by updating quality control records that no spot was found on this sample.

On the other hand, when a spot is visible at step 210, then at step 220 the location of the spot on the paper is marked. For example, a circle may be drawn around the spot on the paper, or any other suitable mark may be made on the paper to indicate the location of the spot. A pencil or other suitable marking tool may be used to mark the paper.

At step 225, a drying process is performed by placing the cigarette on the on the surface 60 in the sample area 67 with the spot pointing toward the lit bulb 20. The cigarette is left in this drying position for a predetermined amount of time, e.g., about a minute or more, to provide ample heat and time for any non-oil spots to evaporate.

At step 230, the cigarette is visually inspected after having been subject to the drying of step 225. The cigarette may be picked up from the surface 60 and visually inspected with the naked eye. The marking applied at step 220 is useful for determining where to look for the spot on the paper.

At step 235, a determination is made as to whether the spot that was initially identified at step 210 is still visible. If the spot is no longer visible, then at step 240 the cigarette is identified as a conforming sample, e.g., by updating quality control records that a non-oil spot was initially detected on this sample prior to drying and that the spot was not detected after drying.

On the other hand, when the spot is determined as still visible at step 235, then at step 245 the paper of the cigarette is separated from the tobacco. This may be performed, for example, by slitting the paper and removing the tobacco rod from the paper.

At step 250, the paper is placed on the viewing surface 80 of the light source 70 with the light source 70 turned on such that the paper is backlit, e.g., light of the light source passes through the viewing surface 80 and the paper.

At step 255, the paper is visually inspected to ascertain the appearance of the spot. For example, while the paper is backlit by the light source, the spotted area of the paper is compared to a non-spotted area of the paper to determine whether the spotted area has a translucent and/or transparent appearance relative to the non-spotted area. Thus, step 255 may constitute visually inspecting an appearance of the paper at the spot relative to an unspotted portion of the paper.

At step 260, a determination is made as to whether the spotted area has a translucent and/or transparent appearance based on the inspection of step 255. Thus, step 260 may constitute determining the spot is one of an oil spot and a non-oil spot based on the visually inspecting the appearance of the paper at the spot relative to the unspotted portion of the paper. For example, when the spot does not appear translucent and/or transparent, e.g., the spotted area appears opaque, then at step 265 the cigarette is identified as a conforming sample, e.g., by updating quality control records that a non-oil spot was detected on this sample.

On the other hand, when the spot does appear translucent and/or transparent, then at step 270 the cigarette is identified as a nonconforming sample, e.g., by updating quality control records that an oil spot was detected on this sample. At step 275 the cigarette is flagged for further analysis, such as non-conforming product investigation and lab analysis to determine the source of the spot.

As may be appreciated, the methods, systems and field test kits disclosed herein also have utility in detecting oil spots on unfinished cigarettes and other types of smoking articles (e.g. cigars, and any other wrapped articles comprising a material wrapped in an oil-absorbing web) and are within the scope and spirit of the present disclosure in its aspects, as those skilled in the art will understand.

The particulars shown herein are by way of example and for purposes of illustrative discussion only and are presented in the cause of providing what is believed to be the most useful and readily understood description of the principles and conceptual aspects. In this regard, no attempt is made to show structural details in more detail than is necessary for fundamental understanding, the description taken with the drawings making apparent to those skilled in the art how the several forms disclosed herein may be embodied in practice.

It is noted that the foregoing examples have been provided merely for the purpose of explanation and are in no way to be construed as limiting. While aspects have been described with reference to an exemplary embodiment, it is understood that the words which have been used herein are words of description and illustration, rather than words of limitation. Changes may be made, within the purview of the appended claims, as presently stated and as amended, without departing from the scope and spirit of the present disclosure in its aspects. Although aspects have been described herein with reference to particular means, materials, and/or embodiments, the present disclosure is not intended to be limited to the particulars disclosed herein; rather, it extends to all functionally equivalent structures, methods and uses, such as are within the scope of the appended claims.

What is claimed:

1. A system for differentiating between oil spots and non-oil spots in a wrapped article comprising a web and a wrapped material, the system comprising:
   a heat source comprising a heat lamp bulb that applies heat to the wrapped article for a predetermined amount of time when the wrapped article is placed in a sample area on a surface that is arranged at a predetermined distance away from a heating element of the heat source; and
   a light source that provides backlighting to the web of the wrapped article when the web has been separated from the wrapped material portion and placed on a viewing surface of the light source.

2. The system of claim 1, wherein the light source comprises a base, at least one fluorescent light tube within the base, and the viewing surface connected to the base and arranged over the at least one fluorescent light tube.

3. The system of claim 2, wherein the viewing surface is composed of a material that transmits and diffuses light emanating from the at least one fluorescent light tube.

4. The system of claim 1, wherein the light source is configured to backlight the web placed on the viewing surface such that:
   an oil spot on the web appears translucent and/or transparent compared to a unspotted portion of the web; and
   a non-oil spot on the web appears opaque compared to the unspotted portion of the web.

5. The system of claim 1, wherein the light source is configured to backlight the web placed on the viewing surface such that:
   a relatively translucent and/or transparent spot on the web is indicative of an oil spot; and
   a relatively opaque spot on the web is indicative of a non-oil spot.

6. The system of claim 1, wherein:
   the predetermined amount of time is at least one minute; and
   the predetermined distance is about 8 inches.

7. The system of claim 1, wherein the wrapped article is a finished cigarette comprising paper wrapped around a tobacco portion.

8. A method comprising visually inspecting a finished cigarette for oil spots using the system of claim 1.

9. The system of claim 1, wherein said heat lamp bulb is an incandescent light bulb.

10. A method for differentiating between oil spots and non-oil spots in a wrapped article comprising a web and a wrapped material, the method comprising:
    obtaining a wrapped article from a production line;
    detecting a visible spot on the web;
    drying the wrapped article using a heat source for a predetermined amount of time; and
    visually inspecting the wrapped article for the spot after the drying.

11. The method of claim 10, wherein the drying comprises placing the wrapped article in a sample area on a surface that is arranged at a predetermined distance away from a heating element of the heat source for the predetermined amount of time.

12. The method of claim 11, wherein:
    the predetermined amount of time is at least one minute; and
    the predetermined distance is about 8 inches.

13. The method of claim 10, further comprising marking the web around the spot prior to the drying to facilitate looking for the spot after the drying.

14. The method of claim 10, wherein the detecting the visible spot on the web comprises visually inspecting the wrapped article.

15. The method of claim 10, further comprising visually detecting the spot after the drying.

16. The method of claim 15, further comprising:
    separating the web from the wrapped material portion; and
    visually inspecting an appearance of the web at the spot relative to an unspotted portion of the web.

17. The method of claim 16, further comprising backlighting the web while visually inspecting the appearance of the web at the spot relative to the unspotted portion of the web.

18. The method of claim 17, wherein the backlighting comprises placing the web on a viewing surface of a light source.

19. The method of claim 18, further comprising setting up a system comprising the heat source and the light source prior to the drying.

20. The method of claim 16, further comprising determining the spot is one of an oil spot and a non-oil spot based on the visually inspecting the appearance of the web at the spot relative to the unspotted portion of the web.

21. The method of claim 16, further comprising:
    identifying the spot as an oil spot when the web at the spot is translucent or transparent relative to the unspotted portion of the web; and
    identifying the spot as a non-oil spot when the web at the spot is opaque relative to the unspotted portion of the web.

22. The method of claim 16, further comprising:
    determining the spot is an oil spot based on the visually inspecting the appearance of the web at the spot relative to the unspotted portion of the web; and performing additional analysis on the web at the spot to determine a source of the oil.

23. The method of claim 10, wherein the wrapped article is a finished cigarette comprising paper wrapped around a tobacco portion.

24. A field test kit for differentiating between oil spots and non-oil spots in a wrapped article comprising a web and a wrapped material, the field test kit comprising:
 a heat source comprising a heat lamp bulb that applies heat to the wrapped article for a predetermined amount of time when the wrapped article is placed in a sample area on a surface that is arranged at a predetermined distance away from a heating element of the heat source; and
 a light source that provides backlighting to the web of the wrapped article when the web has been separated from the wrapped material and placed on a viewing surface of the light source.

25. The field test kit of claim 24, wherein the wrapped article is a finished cigarette comprising paper wrapped around a tobacco portion.

26. The field test kit of claim 25, wherein the light source is configured to backlight the paper placed on the viewing surface such that:
 an oil spot on the paper appears translucent and/or transparent compared to a unspotted portion of the paper; and
 a non-oil spot on the paper appears opaque compared to the unspotted portion of the paper.

27. The field test kit of claim 25, wherein the light source is configured to backlight the paper placed on the viewing surface such that:
 a relatively translucent and/or transparent spot on the paper is indicative of an oil spot; and
 a relatively opaque spot on the paper is indicative of a non-oil spot.

28. The field test kit of claim 24, wherein the light source comprises a base, at least one fluorescent light tube within the base, and the viewing surface connected to the base and arranged over the at least one fluorescent light tube.

29. The field test kit of claim 28, wherein the viewing surface is composed of a material that transmits and diffuses light emanating from the at least one fluorescent light tube.

30. The field test kit of claim 24, wherein:
 the predetermined amount of time is at least one minute; and
 the predetermined distance is about 8 inches.

31. A method comprising visually inspecting a finished cigarette for oil spots using the field test kit of claim 24.

32. The field test kit of claim 24, wherein said heat lamp bulb is an incandescent light bulb.

33. A system for differentiating between oil spots and non-oil spots in a wrapped article comprising a web and a wrapped material, the system comprising:
 a heat source that applies heat to the wrapped article for a predetermined amount of time when the wrapped article is placed in a sample area on a surface that is arranged at a predetermined distance away from a heating element of the heat source; and
 a light source that provides backlighting to the web of the wrapped article when the web has been separated from the wrapped material portion and placed on a viewing surface of the light source, wherein the light source is configured to backlight the web placed on the viewing surface such that:
 an oil spot on the web appears translucent and/or transparent compared to a unspotted portion of the web; and
 a non-oil spot on the web appears opaque compared to the unspotted portion of the web.

34. A system for differentiating between oil spots and non-oil spots in a wrapped article comprising a web and a wrapped material, the system comprising:
 a heat source that applies heat to the wrapped article for a predetermined amount of time when the wrapped article is placed in a sample area on a surface that is arranged at a predetermined distance away from a heating element of the heat source; and
 a light source that provides backlighting to the web of the wrapped article when the web has been separated from the wrapped material portion and placed on a viewing surface of the light source, wherein the light source is configured to backlight the web placed on the viewing surface such that:
 a relatively translucent and/or transparent spot on the web is indicative of an oil spot; and
 a relatively opaque spot on the web is indicative of a non-oil spot.

35. A method for differentiating between oil spots and non-oil spots in a wrapped article comprising a web and a wrapped material, the method comprising:
 obtaining a wrapped article from a production line;
 detecting a visible spot on the web;
 drying the wrapped article using a heat source for a predetermined amount of time;
 visually inspecting the wrapped article for the spot after the drying;
 visually detecting the spot after the drying;
 separating the web from the wrapped material portion;
 visually inspecting an appearance of the web at the spot relative to an unspotted portion of the web;
 identifying the spot as an oil spot when the web at the spot is translucent or transparent relative to the unspotted portion of the web; and
 identifying the spot as a non-oil spot when the web at the spot is opaque relative to the unspotted portion of the web.

36. A method for differentiating between oil spots and non-oil spots in a wrapped article comprising a web and a wrapped material, the method comprising:
 obtaining a wrapped article from a production line;
 detecting a visible spot on the web;
 drying the wrapped article using a heat source for a predetermined amount of time;
 visually inspecting the wrapped article for the spot after the drying;
 visually detecting the spot after the drying;
 separating the web from the wrapped material portion;
 visually inspecting an appearance of the web at the spot relative to an unspotted portion of the web;
 determining the spot is an oil spot based on the visually inspecting the appearance of the web at the spot relative to the unspotted portion of the web; and
 performing additional analysis on the web at the spot to determine a source of the oil.

37. A field test kit for differentiating between oil spots and non-oil spots in a wrapped article comprising a web and a wrapped material, the field test kit comprising:
 a heat source that applies heat to the wrapped article for a predetermined amount of time when the wrapped article is placed in a sample area on a surface that is arranged at a predetermined distance away from a heating element of the heat source; and
 a light source that provides backlighting to the web of the wrapped article when the web has been separated from the wrapped material and placed on a viewing surface of the light source, wherein the light source is configured to backlight the paper placed on the viewing surface such that:

an oil spot on the paper appears translucent and/or transparent compared to a unspotted portion of the paper; and a non-oil spot on the paper appears opaque compared to the unspotted portion of the paper; and wherein the wrapped article is a finished cigarette comprising paper wrapped around a tobacco portion.

38. A field test kit for differentiating between oil spots and non-oil spots in a wrapped article comprising a web and a wrapped material, the field test kit comprising:

a heat source that applies heat to the wrapped article for a predetermined amount of time when the wrapped article is placed in a sample area on a surface that is arranged at a predetermined distance away from a heating element of the heat source; and a light source that provides backlighting to the web of the wrapped article when the web has been separated from the wrapped material and placed on a viewing surface of the light source, wherein the light source is configured to backlight the paper placed on the viewing surface such that:

a relatively translucent and/or transparent spot on the paper is indicative of an oil spot; and a relatively opaque spot on the paper is indicative of a non-oil spot; and wherein the wrapped article is a finished cigarette comprising paper wrapped around a tobacco portion.

* * * * *